United States Patent [19]

Offenbacher et al.

[11] Patent Number: 5,091,800
[45] Date of Patent: Feb. 25, 1992

[54] COVER LAYER FOR OPTICAL ION SENSORS

[75] Inventors: Helmut Offenbacher, Graz; Erna Schwarzenegger, Semriach, both of Austria

[73] Assignee: AVL AG, Schaffhausen, Austria

[21] Appl. No.: 216,546

[22] Filed: Jul. 8, 1988

[30] Foreign Application Priority Data

Jul. 20, 1987 [AT] Austria ................. 1833/87

[51] Int. Cl.$^5$ ............................................. G01N 21/63
[52] U.S. Cl. .................................. 359/350; 359/896; 250/462.1; 356/412; 436/172; 435/808; 210/500.25; 210/500.3; 73/36
[58] Field of Search ............... 350/1.7, 316, 319, 321; 435/808, 817; 430/4, 939; 356/38, 39, 412; 436/163, 172; 128/634, 636; 210/500.25, 500.3, 500.43, 505; 204/98; 250/462.1; 73/36

[56] References Cited

U.S. PATENT DOCUMENTS

| | | | |
|---|---|---|---|
| 3,846,236 | 11/1974 | Updike | 435/2 |
| 3,996,141 | 12/1976 | Updike | 210/501 |
| 4,244,824 | 1/1981 | Lange et al. | 210/500.25 |
| 4,484,987 | 11/1984 | Gough | 435/817 |
| 4,529,495 | 4/1985 | Marsoner | 204/411 |
| 4,548,907 | 10/1985 | Seitz et al. | 436/163 |
| 4,568,518 | 2/1986 | Wolfbeis et al. | 427/157 |
| 4,579,808 | 4/1986 | Held | 430/4 |
| 4,587,101 | 5/1986 | Marsoner et al. | 250/462.1 |
| 4,597,392 | 7/1986 | Opitz et al. | 356/39 |
| 4,703,757 | 11/1987 | Cohen | 128/675 |
| 4,755,299 | 7/1988 | Brüschke | 210/500.43 |
| 4,798,738 | 1/1989 | Yafuso et al. | 427/164 |
| 4,801,655 | 1/1989 | Murray, Jr. et al. | 525/329.4 |

FOREIGN PATENT DOCUMENTS 380957 8/1986 Austria .
381592 11/1986 Austria .

*Primary Examiner*—Bruce Y. Arnold
*Assistant Examiner*—R. D. Shafer
*Attorney, Agent, or Firm*—Watson, Cole, Grindle & Watson

[57] ABSTRACT

In order to eliminate interferences of an optical or chemical nature, preferably in optical sensors, a cover layer is provided which comprises a hydrophilic, ion-permeable polymer membrane containing precious metal pigments deposited by a reduction or reduction/-cementation technique for the purpose of suppressing straylight.

8 Claims, 2 Drawing Sheets

COVER LAYER FOR OPTICAL ION SENSORS

BACKGROUND OF THE INVENTION

The present invention relates to a cover layer preferably to be applied on the sample side of optical ion sensors, and to a method of preparing such a layer.

In clinical applications of analytical chemistry optical sensors have become increasingly important over the last few years; among other advantages, they are easier to miniaturize than conventional electrochemical sensors.

Optical sensors, so-called "optodes", essentially are transparent substrates on which indicators based on absorption dyes or fluorescent dyes are immobilized both chemically and physically.

The functional principle of such sensors is based on the specific interaction between the species to be analyzed and the indicator, and on the subsequent changes in the light-absorbing or fluorescent properties of the indicator—depending on the type of indicator used.

DESCRIPTION OF THE PRIOR ART

Such sensors are described in Austrian Patent No. 381,592 for instance, and are based on reflectance measurement, i.e., the filtered light of a light source is transmitted via an optical waveguide onto the sensitive layer of the optical sensor carrying the indicator. During the measuring process the sensitive layer is in contact with the sample in the measuring chamber, and—depending on the concentration of the species to be analyzed—the indicator, for example an absorption dye, will react by a change in the intensity of the reflected light. The reflected light, i.e., fluorescent light in the instance of a fluorescent indicator, is passed to a detector via an optical filter, and is transformed into an electric measuring signal.

During this process interferences both of an optical and a chemical nature may occur unless suitable action is taken. Optical interferences mainly are fluctuations in light intensitiy, which are independent of the concentration of an analyte, but are caused by light interaction with the sample, or, more generally, with the sensor environment. Examples are the incident radiation of ambient light in the sensor and light detection area, light absorption and scattering in the sample to be analyzed, fluorescent of the sample itself, and changes in the conditions of reflexion at the sensor/sample interface due to the variations in the refractive index of the sample.

All of these phenomena may influence the measuring signal which is received as a light intensity depending on the analyte.

Interferences of a chemical nature are explained as is following. With optical sensors, indicators immobilized on the surface of a substrate often are directly contacted with the sample medium, for instance if ionic species are to be analyzed, as in pH measurement.

Major influencing factors of an unspecific nature are the ionic strength of a sample, and charged macromolecules, for instance proteins, which may affect the measuring signals and cause considerably errors of measurement.

In a former proposal a technique is decribed, in which a cover layer is applied to the surface of a sensor, which determines the microenvironment of the indicator on the sensor surface and largely reduces influences due to the ionic strength of the sample, for instance. The "protein" error caused by charged macromolecules, however, can be prevented only by protecting the surface of the sensor against proteins.

SUMMARY OF THE INVENTION

It is an object of this invention to propose a cover layer which is impervious to light in the spectral range of the light to be detected, preferably for application on the sample side of optical ion sensors, in order to prevent the above optical and chemical interferences, without affecting the interaction between analyte and indicator. In addition, the rise-time of the sensor element is not to be affected.

In the invention this is achieved by using a hydrophilic, ion-permeable polymer membrane as a cover layer, which contains pigments of precious metals precipitated by a reduction or reduction/cementation technique for the purpose of suppressing straylight. The vast majority of hydrophilic polymer membranes or polymer foils are characterized by good permeability to ionic or polar substances—with various limiting molecular weights—which may often be adjusted by a suitable manufacturing process. For depositing of the precious metal pigments by a reduction technique the polymer membrane is treated with a precious metal salt solution and a suitable reducing agent. In a subsequent cementation process silver particles may be replaced by gold particles after treatment with aurous hydroxide, for example. The cover layer obtained in this manner will retain its mechanical and ion-selective properties in addition to being impervious to straylight in the wavelength range of the light to be detected.

A criterion of the mechanical stability of a hydrophilic polymer membrane is given by its insolubility in water and ion-containing solutions, and by the retaining of its strength and elasticity upon contact with these media. Permeability to water and ions is ensured and indicated by the swelling behaviour of the hydrophilic membranes.

A major criterion of the hydrophilic and ion-permeable properties of a mechanically stable foil is the presence of polar and/or ionic groups in the polymer structure (for example, —OH, —CONHR, —OR, —NH$_2$, —NR$_2$, —COO$^-$, —SO$_3^-$, —NH$_3^+$, —NH$_3^+$, etc.). These groups need not be present as side-groups of the polymer structure, but may be integrated into it.

The cover layer described by the invention may also be used for other applications, for instance for catalytic purposes, or in other areas in which boundary layers of selective ion-permeability are required, which are impervious to light at the same time.

According to the invention it is preferable for the hydrophilic ion-permeable polymer membrane to have a high molecular weight and/or cross-linkages and/or to be in a partly crystalline state. The required properties of the membrane, such as water-insolubility and selective ion-permeability are particularly well developed in hydrophilic polymers of a high molecular weight, for instance, or in cross-linked hydrophilic polymers or partly crystalline polymers. The partly crystalline state is characterized by a given orientation of the polymer molecules, which may be obtained by stretching.

In such instances it is preferable for the hydrophilic ion-permeable polymer membrane to be made of regenerated cellulose ("cellophane"), or for-the hydrophilic ion-permeable polymer membrane to be made of a cross-linked or stretched polyvinyl alcohol, pigments of precious metals from the group of Ag, Au, Pt being embedded in the hydrophilic ion-permeable polymer membrane in colloidal distribution.

In a further development of the invention the hydrophilic, ion-permeable polymer membrane containing pigments of precious metals is provided with an indicator in homogeneous distribution.

By attaching the cover layer obtained in this way onto a transparent sensor carrier or the end of a light guide, a sensor is obtained which is suitable for a specific ionic species depending on the selectivity of the indicator.

For pigmentation of the above polymer membrane of regenerated cellulose, for example, conventional methods, such as the addition of the pigment to the prepolymer and subsequent stretching, cannot be employed, since such a method would lead to a loss of essential properties of the membrane, such as mechanical stability.

Besides, processes such as dyeing by chemical immobilization of the dyes or by applying direct azo dyes, will degrade the mechanical properties of cellophane foils in particular, and drastically reduce permeability to ions, especially to hydronium ions.

The decrease in ion permeability is due to the decrease in hydrophilic properties caused by chemical modification or the addition of the essentially non-polar dye.

A method of preparing a cover layer according to the invention provides that a hydrophilic, ion-permeable polymer membrane be prepared, and that this membrane be treated with one or more dissolved salts of a precious metal from the group of Ag, Au, Pt as well as with one or more reducing agents, such that the pigment of the respective precious metal is integrated into the polymer membrane in colloidal distribution. It has turned out unexpectedly that cover layers conforming to the requirements of this invention are obtained by embedding colloidal precious metals in the prefabricated hydrophilic polymer membrane by means of a reduction or reduction/cementation technique.

It has further turned out that upon application together with the reducing agent the process of reduction of the precious metal salts takes place more rapidly in the foil itself than in the applied solution, which will protect the foil from the formation of a "mirror coat" and the subsequent loss of its permeability to the analyte.

For the purpose of precious metal colloid pigmentation the salts of silver, gold and platinum are particularly suited; suitable reducing agents are those conventionally used for the specific precious metals. The reduction of silver salt is best performed using substances with aldehyde function.

In addition to the reductive integration of colloidal precious metals it is also possible to transform non-precious metal colloids deposited onto the cellophane foil into precious metal colloid pigments via a cementation technique.

Reductive precious metal colloid pigmentation may be performed in several ways; e.g., a solution of the precious metal salt and a solution of the reducing agent may be applied in turn on the hydrophilic, ion-permeable polymer membrane by dipping, spraying or painting; if required, the polymer membrane may be dried after each treatment with the precious metal salt solution.

If a dipping technique is employed, the polymer membrane in turn is immersed in the metal salt solution and the reducing agent. Due to these alternating baths, however, the reagents may be carried over and metal nuclei may form as a consequence both in the precious metal salt bath and in the reducing bath. The occurence of metal nuclei in the bath fluids will inhibit preparation of the cover layer, as the reduction of the metal salts together with the rapid growth of the nuclei in the immediate vicinity of the foil will inhibit deposition of metal colloids in the foil itself. Such baths will soon become inactive due to the "poisoning" with metal nuclei, which will entail a large consumption of precious metal salts and high costs.

If a spraying technique is employed, the precious metal salt solution and a suitable, strong reducing agent are sprayed onto the foil in alternating order. With this technique the foil should be allowed to dry after spraying on the precious metal salt solution, which will enhance concentration of the precious metal ions in the foil. In this instance the formation of colloids will set in as soon as the reducing agent is sprayed onto the foil.

The colloidal gold foils prepared with this technique, for instance, are characterized by transparency and a light blue coloring, which indicates that the particle size of the precipitated gold probably is greater than several thousand atomic layers.

For preparation of a colloidal silver foil the invention provides that a polymer membrane, preferably of regenerated cellulose, be treated with a solution of the precious metal salt $AgNO_3$ and a glucose or formaldehyde solution as a reducing agent.

Following are two examples of preparing colloidal silver foils.

(1) A cellophane foil put on a frame while wet is dipped in turn into a 2% solution of silver nitrate with an excess of ammonia and into a semiconcentrated solution of formaldehyde. Prior to each change of bath the excess solution adhering to the foil is removed with absorbent filter paper. After 3 to 5 alternating baths the foil is perfectly opaque in the visible spectral range.

After a thorough rinse with ammonia water the foil is allowed to dry slowly in its frame. In order to improve the mechanical properties of the dry foil a small quantitiy of ethylene glycol or glycerol is added to the rinsing water.

(2) Solutions of silver nitrate and ammoniac glucose, or ammoniac silver nitrate and formaldehyde are sprayed alternatingly onto a cellophane foil that has been attached while wet, the foil being allowed to dry between individual sprayings, or the metal salt solution and the reducing agent being applied on opposite sides of the foil. In either case total light-absorption in the range of wavelengths used for analysis is reached after 1 to 3 sprayings.

For preparation of a foil of colloidal platinum the invention provides that a polymer membrane, preferably of regenerated cellulose, be treated with a solution of hexachloroplatinic acid and a solution of tin(II) as a reducing agent. For this purpose a 5% solution of hexachloroplatinic acid in methanol/water is applied onto a cellophane foil that has been attached while wet. After slow drying a 5% acid or alkaline tin(II) solution is sprayed on and the membrane coated in this manner is allowed to rest for one hour at 50° C. The translucent brown foil is perfectly opaque in the wavelength range of 200 to 480 nm, at 800 nm transmission does not exceed 60%.

According to the invention, another method of reductive precious metal colloid pigmentation is provided by applying a combined solution of the precious metal salt and the reducing agent onto the hydrophilic, ion-permeable polymer membrane by dipping, spraying or brushing techniques, and by rinsing off any metal granules remaining on the surface after the precious metal pigments have been reduction-deposited on the polymer membrane. For this purpose small doses of the precious metal salt solution are mixed with a weak reducing agent and sprayed onto the foil that has been attached while wet; the assembly is then left to rest at room temperature or at a higher temperature, the reduction process leading to precious metal precipitation predominantly in the foil. Reduction in the liquid film adhering to the foil leads to the deposition of metal granules which may easily be rinsed off.

In a further development of the invention the polymer membrane, preferably made from regenerated cellulose, is sprayed with an aqueous solution of silver nitrate and D-glucose, and is left to dry in a container in ammonia atmosphere, the temperature being raised to 50° C. preferably. For preparation of a colloidal silver foil according to this method a cellophane foil which has been put on a frame while wet, is sprayed with a solution of 1 g silver nitrate, 3 g D-glucose and 10 ml water. After a period of drying the coated foil is transferred to a closed container with a few milliliters of concentrated ammonia. The ammonia-enriched atmosphere will accelerate reduction of the silver ions in the foil, further acceleration being possible by raising the temperature to, say, 50° C.

With this method the foil assumes a brown color as soon as ammonia is added, which will darken within a period of 30 minutes to 24 hours, depending on the temperature; this process may be monitored photometrically. The depositing of silver in the reaction layer adhering to the foil occurs with a delay and will lead to the formation of fine granular material which can easily be removed by rinsing.

For the economic preparation of opaque foils of colloidal gold, the invention provides that silver pigments be reduction-deposited in the hydrophilic, ion-permeable membrane and that they be replaced by gold pigments in a cementation process, the hydrophilic, ion-permeable membrane being contacted with a solution of tetrachloroauric acid during the cementation process. Progress in cementation, i.e., the precipitating of gold on the silver particles and the simultaneous dissolving of the latter, is monitored by observing the foils in passing light and noting a change of color from an initial dark red-brown to a dark violet. This kind of precious metal pigmentation also has cost advantages. Opaque membranes require a sufficiently high content of colloidal precious metal in the polymer matrix. This is achieved by the presence of sufficiently high concentrations of precious metal ions in the membrane material after swelling, i.e., by immersing it in concentrated precious metal salt solutions. The cementation-induced precipitation of metals with strongly positive redox potential on less precious ones is already achieved at low concentrations of the precious metal salt. Since gold and platinum salts are much more expensive than silver nitrate, the preparation of cover layers of high chemical resistance by means of cementation constitutes an elegant method; thus an increase in both reaction time and reaction temperature will reduce the consumption of gold or platinum salts by the factor $10^2$.

A foil of colloidal gold is prepared as follows A cellophane foil pigmented with colloidal silver is immersed for two hours in a 2% methanolic solution of tetrachloroauric acid, with no light permitted during this period, and is then rinsed with diluted ammonia in order to remove the silver chloride deposited in the foil during the reaction process.

The invention may further provide that the hydrophilic, ion-permeable polymer membrane be prepared by drying a solution of polyvinyl alcohol applied as a film and by exposing this film to vapors of glutaric-aldehyde for the purpose of chemical cross-linking. For example, a 5% solution of polyvinyl alcohol is applied as a film to a thickness of 200 μm and is then dried at a temperature not exceeding 50° C., thus forming a foil with a thickness of 10 μm. This foil is then treated with glutaric aldehyde vapors for the purpose of cross-linking based on acetalation, and is pigmented with colloidal silver after having been rinsed and put on a frame, such that a flexible membrane is produced which is characterized by a dark brown color and good capability of swelling in water.

According to the invention an indicator in homogeneous distribution may be added to the polymer membrane in a known manner after integration of the precious metal pigments.

For this process both the colloidal precious metal, which is optically de-coupling, and subsequently the indicator are bonded to a hydrophilic or ion-permeable polymer membrane by chemical immobilization, as described in Austrian Patent No. 380,957 for instance. In this way a sensor foil is obtained which is not affected by interferences due to ambient light nor by the "protein error".

A sensor foil with the above characteristics also is obtained if both the colloidal precious metal and the fluorescence-optical indicator are present in the membrane in homogeneous distribution—the latter attached via chemical immobilization. Care should be taken, however, that the amount of colloidal precious metal deposited—while rendering the assembly impervious to light from outside of the wavelengths used in analysis—will permit sufficient penetration of this light into the membrane on the side of the sensor.

In order to improve the light yield and thus the test signal in this kind of sensor foils, the layers of the selected membranes should be relatively thick, i.e., thicker than 10 μm.

Precipitation of the precious metal pigments during reaction may be monitored over time by means of optical devices similar to a photometer, and may be stopped by rinsing once a defined value of transmission has been attained for a wavelength depending on the precious metal to be integrated.

Definition of this transmission value will depend on the thickness of the membrane layer, on the type of indicator used and on the area-concentration of the indicator and thus the method of immobilization.

Because of the aggressiveness of the reaction products obtained during precious metal reduction the process of indicator immobilization is best performed after the reaction of precious metal colloid pigmentation.

Following is an example describing the preparation of a cover layer containing an indicator.

A cellophane foil is prepared by taking a hydrophilic, ion-permeable polymer membrane, comprising regenerated cellulose and treating it with a solution of $AgNO_3$ and a glucose agent as the reducing agent to obtain a foil of colloidal silver. The reaction process is stopped by rinsing with water when a transmission of 5% (measured at 600,$\mu$m) has been reached. After drying the dye is immobilized as described in Austrian Patent No. 380,957. For this purpose the foil is immersed for two days in a 40% solution of polyethylene imine, following which it is rinsed with water for one minute and left to dry over KOH or calcium oxide. The dry amino-modified foil is contacted for one minute with a solution of 0.5 mg 1-acetoxypyrene-3,6,7-trisulphonylchloride in 10 ml dioxan and dipped into a 5% solution of sodium hydrogencarbonate after a rinse with dioxan and water. After rinsing with water and drying at room temperature the sensor membrane is ready for use.

BRIEF DESCRIPTION OF THE DRAWING

Following is a further description of the invention as illustrated by the accompanying drawing, in which.

DETAILED DESCRIPTION OF THE PREFERRED EMBODIMENT

Figure 1:
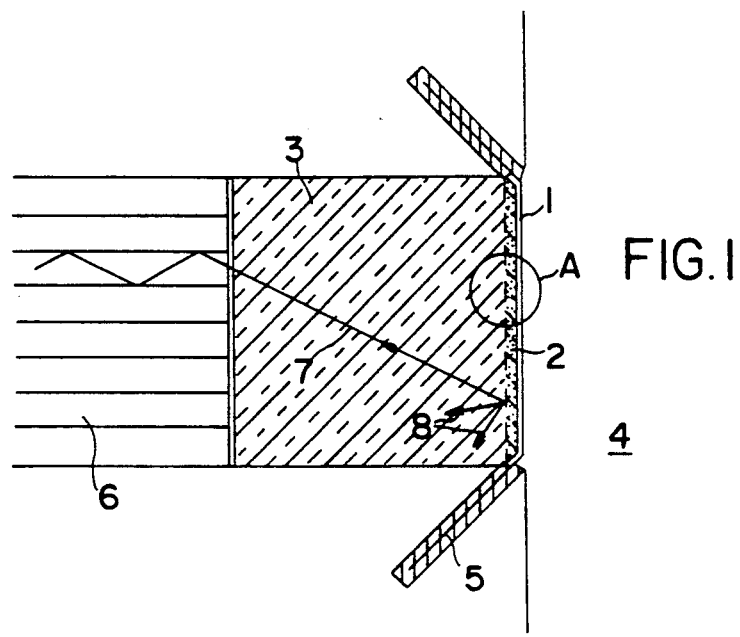
FIG. 1 is a schematic view of a cover layer according to the invention, which is applied on an optical ion sensor.

In FIG. 1 a pH sensor is coated with a hydrophilic, ion-permeable polymer membrane 1 of the type described, i.e., in such a way that the polymer membrane 1 is situated between the sensitive layer 2 of the sensor 3 and the sample chamber 4. The membrane 1 is attached by conventional techniques, such as mechanical clips, tautening by an O-ring, or, preferably, double-face bonding in a peripheral area 5 outside of the sensitive zone of the sensor.

The optical fiber system 6 and the excitation radiation 7 as well as the reflection or fluorescence radiation 8 are mentioned here for the sake of completeness.

Figure 2A:
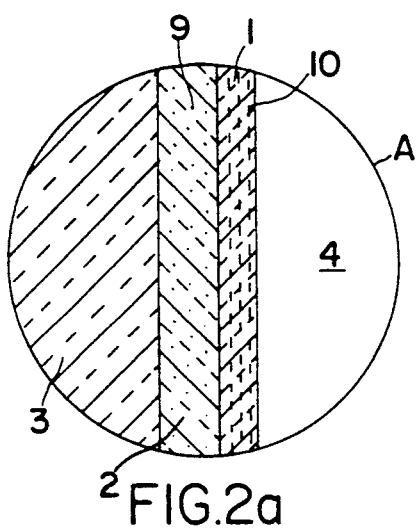
FIGS. 2a and 2b shows the details of the cover layer in FIG. 1, and FIGS. 3 to 6 give transmission spectra of the cover layer as described.

FIG. 2a shows, in an enlarged scale, a part of the sensitive layer 2 containing the homogeneous distributed indicator 9 and the adjoining polymer membrane 1 containing the precious metal pigments 10.

Figure 2B:
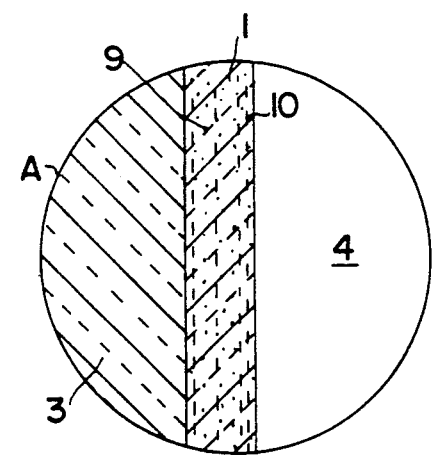

As is shown in FIG. 2b, the indicator 9 may be directly added to the polymer membrane 1 by conventional techniques, in which instance the sensitive layer 2 of the sensor 3 is not needed. The uses and properties of the cover layer described above for optical pH sensors also apply to sensors for other ionic species in an analogous way.

In the diagrams of FIGS. 3 to 6 the respective wavelength in nm is plotted on the abcissa, one unit of division corresponding to 100 nm, while transmission in percent is plotted on the ordinate.

Figure 3:
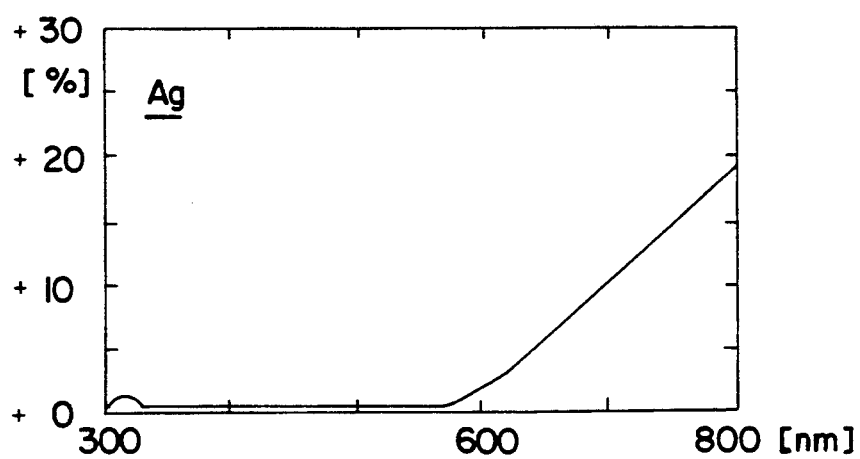
Figure 4:
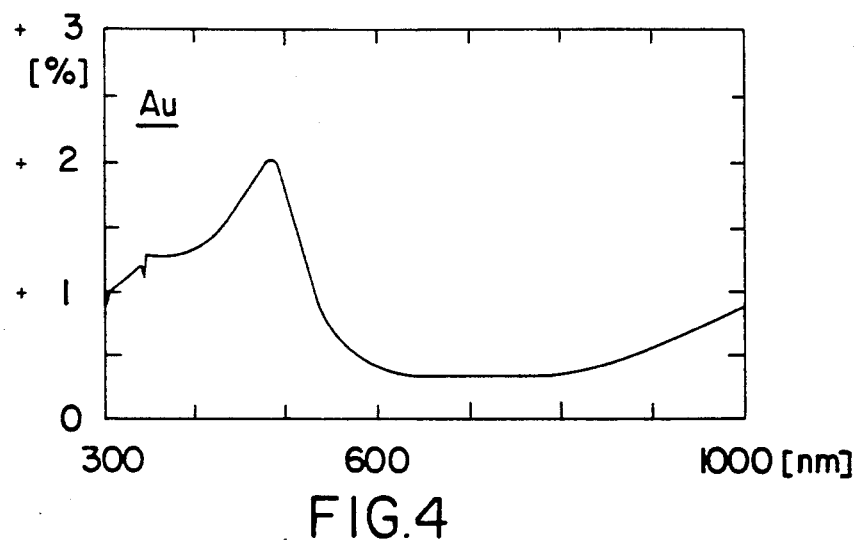
Figure 5:
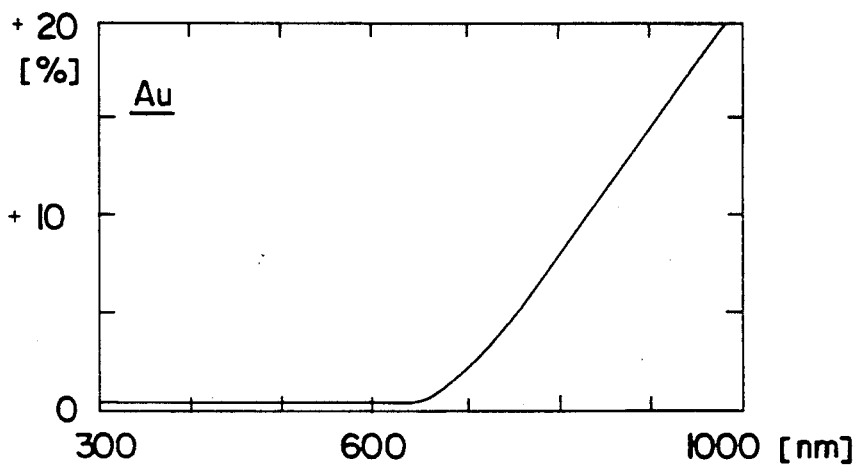
Figure 6:
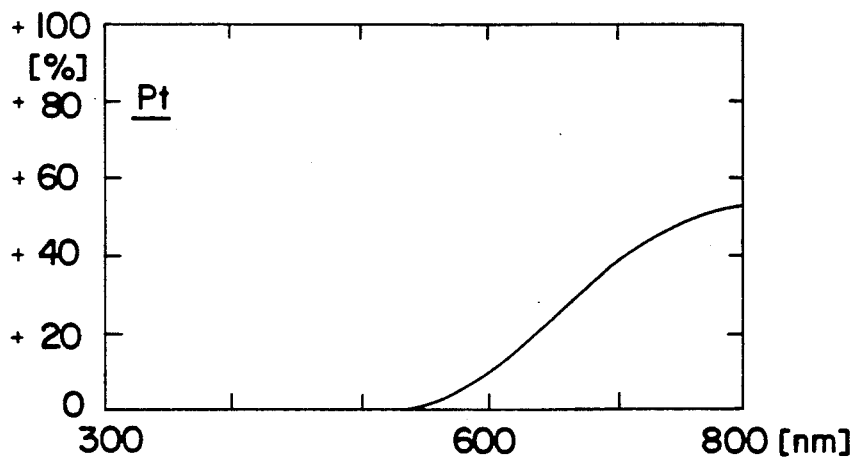

FIG. 3 represents the transmission spectrum of a cellophane foil pigmented with colloidal silver, prepared as in claim 12; FIG. 4 the spectrum of a gold-pigmented cellophane foil prepared as in claim 9; FIG. 5 the spectrum of a cellophane foil pigmented with colloidal gold, prepared as in claim 13; FIG. 6 the transmission spectrum of a cellophane foil pigmented with colloidal platinum as in claim 9.

As can be seen in the transmission spectra FIGS. 3 to 6, the membranes pigmented with colloidal silver or platinum and those pigmented with colloidal gold following the cementation technique are characterized by total absorption in the long-wave ultraviolet range and in the visible range up to 600 nm, whereas the gold foil (FIG. 4) obtained by means of the reduction method, for example by using ascorbic acid as a reducing agent, is characterized by low light transmission in a wavelength range <600 nm, with a transmission maximum at 480 nm.

In order to avoid optical and chemical interferences in optical sensors for analyzing ionic species preference is given to silver- or platinum-pigmented membranes prepared as shown in FIGS. 3 to 6, or gold-pigmented membranes prepared according to FIG. 5.

Interference signals leading to measurement errors, which are caused by optical phenomena or macromolecules in the sample (protein error), can no longer occur in sensors prepared as described. Physico-chemical properties of the sensors regarding the interaction between analyte and optical indicator will not be affected. For instance, identical pH functions and, as a consequence, identical $pk_a$ values (negative decadic logarithm of the acid constant) are found both before and after a cover layer according to the invention has been attached.

We claim:

1. An optical ion sensor having a cover layer for suppressing stray light, said cover layer comprising a hydrophilic, ion-permeable, polymer membrane, having at least one of the following properties: high molecular weight, cross linkages and being in a partly crystalline state, said polymer membrane containing pigments of precious metals from the group consisting of Ag, Au and Pt which are embedded in colloidal distribution and precipitated by reduction techniques.

2. A optical ion sensor according to claim 1, wherein said hydrophilic, ion-permeable polymer membrane is made of regenerated cellulose.

3. A optical ion sensor according to claim 1, wherein said hydrophylic, ion-permeable polymer membrane is made of a cross-linked polyvinyl alcohol.

4. A optical ion sensor according to claim 1, wherein said hydrophilic, ion-permeable polymer membrane is made of a cross-linked stretched polyvinyl alcohol.

5. An optical ion sensor having a cover layer for suppressing stray light, said cover layer comprising a hydrophilic, ion-permeable, polymer membrane, having at least one of the following properties: high molecular weight, cross linkages and being in a partly crystalline state, said polymer membrane containing pigments of precious metals from the group consisting of Ag, Au and Pt, which are embedded in colloidal distribution and precipitated by reduction techniques followed by cementation techniques.

6. An optical ion sensor as claimed in claim 5, wherein said hydrophilic, ion-permeable polymer membrane is made of regenerated cellulose.

7. An optical ion sensor as claimed in claim 5, wherein said hydrophilic, ion-permeable polymer membrane is made of a cross-linked polyvinyl alcohol.

8. An optical ion sensor as claimed in claim 5, wherein said hydrophilic, ion-permeable polymer membrane is made of a cross-linked stretched polyvinyl alcohol.

* * * * *